(12) United States Patent
Hilton et al.

(10) Patent No.: US 6,353,047 B1
(45) Date of Patent: Mar. 5, 2002

(54) RUBBER ADHESION PROMOTERS

(75) Inventors: John Michael Hilton, Bolton; Ian Michael Hawkins, Oldham; Jonathan Colin Wilson, Prestwich, all of (GB)

(73) Assignee: Rhodia Limited, Hertfordshire (GB)

( * ) Notice: Subject to any disclaimer, the term of this patent is extended or adjusted under 35 U.S.C. 154(b) by 0 days.

(21) Appl. No.: 09/529,129

(22) PCT Filed: Oct. 9, 1998

(86) PCT No.: PCT/GB98/03069

§ 371 Date: Jun. 21, 2000

§ 102(e) Date: Jun. 21, 2000

(87) PCT Pub. No.: WO99/19336

PCT Pub. Date: Apr. 22, 1999

(30) Foreign Application Priority Data

Oct. 10, 1997 (GB) .............................................. 9721583
Oct. 24, 1997 (GB) .............................................. 9722513

(51) Int. Cl.$^7$ .......................... C08K 5/04; C08K 5/09; C07F 5/06
(52) U.S. Cl. ......................... 524/398; 524/399; 556/27; 556/51; 556/181; 556/437; 252/182.33; 252/182.35
(58) Field of Search ................................. 524/398, 399; 556/181, 27, 51, 437; 252/182.33, 182.35

(56) References Cited

U.S. PATENT DOCUMENTS 4,137,359 A    1/1979    Bak et al. ................... 428/295

FOREIGN PATENT DOCUMENTS

| DE | 39 10 482 | 10/1990 |
| EP | 0 466 448 | 1/1992 |
| EP | 0 688 780 | 12/1995 |

OTHER PUBLICATIONS

XP–002089268, "Cas Registry Handbook", Chemical Abstracts Service, Columbus, Ohio, RN: 84145–31–3, p. 54RL, (1983).

XP–002089269, "Cas Registry Handbook", Chemical Abstracts Service, Columbus, Ohio, RN: 84176–59–0, p. 80RL, (1983).

*Primary Examiner*—Kriellion A. Sanders
(74) *Attorney, Agent, or Firm*—Finnegan, Henderson, Farabow, Garrett & Dunner, L.L.P.

(57) ABSTRACT

Metal organic compounds comprising three or four atoms of cobalt or nickel, each linked through oxygen atoms to aluminum, silicon or titanium and comprising a combination of aliphatic and aromatic carboxylic acid residues are useful as adhesion promoters to promote the adhesion of brass coated steel to vulcanized rubber.

12 Claims, No Drawings

RUBBER ADHESION PROMOTERS

This invention relates to metal organic compounds, compositions containing them, and their use.

Compounds comprising three atoms of a divalent metal e.g. cobalt, each linked through oxygen atoms to a boron or phosphorus atom and comprising aliphatic monocarboxylic acid residues bonded to the metal are known. Such known compounds have been used as additives to rubber skim stock to improve adhesion of the rubber to metal.

They are provided in a form which is readily handleable, and in particular is not inherently tacky or viscous.

The present invention provides new compounds which have the advantages of the aforesaid known compounds but which improve still further the adhesion of rubber to brass coated steel cord and the retention of such adhesion under conditions of steam and salt ageing, when compared to the known cobalt-containing compounds.

According to the present invention there are provided metal-organic compounds for use in promoting adhesion of rubber to metal, of average formula:

$$X(OMA'_p)_m(OMB'_q)_n$$

in which:

X is Aluminium (Al≣,), Titanium (Ti≣,), Zirconium (Zr≣,), alkyl or aryl silicon (R—Si≣), di-alkyl, di-aryl or alkyl, aryl silicon (R"R"Si≣) or silicon (Si≣);

M is cobalt or nickel, preferably cobalt (II);

A' is an aliphatic carboxylic acid residue (of general formula $R^1COO$) of 7 to 15 carbon atoms;

B' is an aromatic carboxylic acid residue (of general formula RCOO) of 7 to 15 carbon atoms; or an aryloxy substituted aliphatic or aromatic carboxylic acid of 8 to 15 carbon atoms;

p and q are, independently 0.5 to 1.5, preferably 1.0; m+n=x, wherein x is the valency of X, m/n is typically from 0.67 to 9.0, preferably from 1.5 to 4.0;

typically n is 0.2 to (x−1), preferably 0.5 to 3, and especially 0.5 to 1.4.

When X is alkyl- and/or aryl-substituted silicon, the alkyl group is preferably one having 1 to 4 carbon atoms, especially methyl, while the aryl group is preferably phenyl. Typical examples include methylsilicon, dimethylsilicon, diphenylsilicon and methyl, phenylsilicon.

The aliphatic carboxylic acid (A'H) is preferably a mono-carboxylic acid, e.g. n-heptanoic acid, 2,2-dimethylpentanoic acid, 2-ethylpentanoic acid, 4,4-dimethylpentanoic acid, n-octanoic acid, 2,2-dimethylhexanoic acid, 2-ethylhexanoic acid, 4,4-dimethylhexanoic acid, 2,4,4-trimethylpentanoic acid, n-nonanoic acid, 2,2-dimethylheptanoic acid, 6,6-dimethylheptanoic acid, 3,5,5-trimethylhexanoic acid, n-decanoic acid, 2,2-dimethyloctanoic acid, 7,7-dimethyloctanoic acid, n-undecanoic acid, isoundecanoic acid, cekanoic or the mixture of 2,2,2-trialkyl acetic acids known as neodecanoic acid.

The aromatic carboxylic acid (B'—H) may be, for example, benzoic acid, an alkyl-, alkoxy-, amino-, halogen-, thio-, or hydroxy-substituted benzoic acid, such as 2-, 3-, or 4-methylbenzoic acid, salicylic acid, 3,5-diisopropyl salicylic acid, 3,5-di-tertbutyl salicylic acid, anthranilic acid, or 4-chloro-benzoic acid, phthalic acid, terephthalic acid, cinnamic acid, or a more complex aromatic acid comprising a conjugated ring system. When B'—H is an aryloxy substituted acid it is preferably a phenoxysubstituted aliphatic or aromatic acid, especially phenoxyacetic acid and phenoxypropionic acid.

The metal organic compound may be associated with a borate of an element of group IA or IIA of the Periodic Table (ie. an alkali metal or an alkaline earth metal). Said borates may be present at a concentration of up to, say, 20% by weight of the metal compound. Suitable borates include sodium borate, potassium borate, calcium borate and magnesium borate.

The metal organic compound may also be associated with microcrystalline wax and/or process oil, and/or a hydrocarbon resin and/or a resorcinol/formaldehyde resin.

The novel metal organic compounds may be incorporated as adhesion promoters in rubber skim stock comprising rubber and conventional rubber compounding ingredients. The metal organic compound is typically present in an amount from 0.2 to 2 parts by weight per hundred parts by weight of rubber, and preferably the metal organic compound provides about 0.224 parts by weight of cobalt metal per hundred parts by weight of rubber.

The metal organic compounds of the present invention may be made by heating together a mixture in the required proportions of (1) the acids A'H and B'H which give rise to the residues A' and B' as defined above, (2) a source of cobalt or nickel such as the oxide, hydroxide or carbonate, (3) an aluminate, silicate or titanate ester of a lower alcohol, e.g. n-butanol, and (4) an acid capable of forming a volatile ester with the lower alcohol residues present in the said ester, e.g. acetic acid or propionic acid, and distilling off the said volatile ester, preferably under reduced pressure. All of the acids (1) and (4) and the metal source (2) must be pre-reacted before the ester (3) is added. The reaction temperature is typically in the range 50 to 250° C.

The invention is illustrated by the following Examples. Examples 1 to 4 describe the preparation of the new metal organic compounds.

EXAMPLE 1

A solution of cobalt neodecanoate propionate (891 g) in mineral spirits was heated to 50° C. with mechanical stirring. Propionic acid (44 g) and benzoic acid (72.5 g) were added. The reaction mass was stirred for 10 minutes and cobaltous hydroxide (57 g) was added. The reaction mixture was heated slowly to 195° C. and water (24 g) and mineral spirits (446 g) were distilled off, vacuum being used to complete the distillation. Methyltriethoxysilane (126.1 g) was added to the reaction mixture at 170° C. and the reaction held at reflux for 4 hours before ethyl propionate was distilled off as the reaction temperature was raised to 220° C., the distillation being completed by the use of vacuum.

The product (540 g) was a hard brittle blue solid of average formula:

MeSi[OCo(neodecanoate)$_{1.0}$]$_{2.16}$[OCo (benzoate)$_{1.0}$]$_{0.84}$
and contained 22.9% (w/w) cobalt.

EXAMPLE 2

A solution of cobalt neodecanoate propionate (817 g) at 9.8% (w/w) cobalt in mineral spirits was heated to 40° C. with stirring. Propionic acid (44 g) and benzoic acid (71.8 g) were added. To the reaction mass was also added cobaltous hydroxide (55.4 g). The reaction was heated to 190° C., and water and mineral spirits (combined weight 415 g) were distilled off, vacuum being used to complete the distillation.

Aluminium triisopropoxide (132 g) was added slowly and the reaction mass heated to 190° C., distilling off the isopropyl propionate ester as it is formed.

The reaction temperature was slowly raised to 240° C. to distill off any remaining ester, vacuum being used to complete the distillation. A total of 159 g isopropylpropionate was collected.

The product (533 g) was a hard brittle blue solid of average formula:

Al [OCo(neodecanoate)$_{1.0}$]$_{2.1}$[OCo(benzoate)$_{1.0}$]$_{0.9}$ and contained 20.8% w/w cobalt.

EXAMPLE 3

Neodecanoic acid (294 g) propionic acid (188 g) and benzoic acid (88 g) and toluene (200 g) were charged to a reaction flask and heated to 50° C. with mechanical stirring. Cobaltous hydroxide (233 g) was added and the temperature raised to 90° C. to produce a mobile blue liquid. Further heat was applied to remove the water of reaction via a Dean and Stark apparatus, raising the reaction temperature to 190° C. and removing the last traces of solvent under vacuum, yielding 91 g of water and 206 g of toluene. To the reaction mass at 160° C. was slowly added tetrabutyl titanate (205 g) and the reaction was maintained at reflux temperature of 160° C. for 3 hours. Butyl propionate (240 g) was removed by distillation on heating to 230° C., vacuum being used to complete the distillation.

The product (624 g) was a hard brittle blue solid of average formula:

Ti[OCo(neodecanoate)$_{1.0}$]$_{2.8}$[OCo(benzoate)$_{1.0}$]$_{1.2}$ and contained 22.5% (w/w) of cobalt.

EXAMPLE 4

Neodecanoic acid (193 g) benzoic acid (62 g) and toluene (420 g) were charged to a reaction flask equipped with mechanical stirring. To this was added cobaltous hydroxide (156 g) and propionic acid (130 g).

The temperature was raised slowly to 120° C. yielding a viscous blue liquid, the water of reaction being removed using a Dean and Stark apparatus. Further heating was applied to remove the remaining toluene by distillation. At 180° C., vacuum was applied to complete the distillation.

To the reaction mass was slowly added tetraethylorthosilicate (85 g) and the reaction was held at a reflux temperature of 145° C. for 2 hours before ethyl propionate (136 g) was removed by distillation up to a final reaction temperature of 230° C. whereupon vacuum was applied to complete the distillation.

The product (416 g) was a hard brittle blue solid of average formula:

Si[OCo(neodecanoate)$_{1.0}$]$_{2.75}$ [OCo(benzoate)$_{1.0}$]$_{1.25}$ and contained 22.8% (w/w) of cobalt.

Rubber skim stock in accordance with the present invention comprises rubber plus one or more conventional rubber compounding ingredients such as pigments, fillers, extenders, accelerators, antioxidants, vulcanising agents etc., and, as an adhesion promoter, a metal organic compound of the present invention. A rubber skim stock was prepared having the following composition:

|  | Parts by weight |
| --- | --- |
| Natural rubber SMR 10 | 100 |
| Peptiser (RENACIT 12)[a] | 0.05 |
| MAF Carbon Black N-326 | 57 |
| Zinc Oxide | 8 |
| Antidegradant (6 PPD)[b] | 2.0 |
| Accelerator DCBS[c] | 0.7 |
| Insoluble sulphur | 4.0 |

[a] Zinc salt of pentachlorothiophenol
[b] N-(1,3-dimethylbutyl)-N'phenyl-p-phenylene diamine
[c] N,N-Dicyclohexyl-2-benzthiazyl sulphenamide.

Vulcanisable compositions were prepared using the above rubber skim stock and the adhesion promoters listed below. The adhesion promoters were added to the skim stock during mixing in a 15 litre internal laboratory mixer and sheeted off on a Z-roll laboratory mill. All the compositions were vulcanised to T90 plus eight minutes at 1530° C.

Adhesion testing was carried out using a modified static block pull test based upon ASTM D2229 using an embedment length of 10mm. Typical brass coated steel tyre cord of the construction 2+2=X 0.25 from Bekaert was used, each cord having a coating of brass with an average copper content of 63.5%. Adhesion values are quoted in Newtons/10 mm. The results are given in Table 1.

| Ageing Conditions | |
| --- | --- |
| Steam | 16 hours @ 121° C. |
| Humidity | 7 days @ 70° C. 95% RH |
| Heat | 7 days @ 85° C. |
| Salt | 7 days @ R.T., 3.6% w/w NaCl in water. |

The results given in these tables show that rubber skim stock comprising the metal organic compounds of the present invention exhibits substantially improved adhesion of rubber to metal in comparison with known boro neodecanoate compounds. This improvement is particularly marked under conditions of steam ageing. Additionally, the new metal organic compounds exhibit equivalent performance at lower usage levels than the corresponding boro neodecanoates.

In one embodiment the metal compound is deposited on a support, for example from an oil solution of the compound. The support is typically silica or a silicate of a Group IA of IIA metal such as sodium silicate, potassium silicate, magnesium silicate or calcium silicate.

TABLE 1

Adhesion Test results

| Compound | Co Addition level, parts per hundred rubber in skim stock | Adhesion test condition | | | | |
| --- | --- | --- | --- | --- | --- | --- |
| | | Unaged | Heat Aged | Humidity aged | Steam aged | Salt aged |
| Control | 0.000 | 19.8 | 21.8 | 22.2 | 28.8 | 20.6 |
| Cobalt boro neodecanoate ([Manobond] MANOBOND C22.5) | 0.224 | 37.2 | 35.7 | 33.8 | 15.4 | 33.2 |
| | 0.150 | 40.2 | 33.0 | 39.3 | 27.2 | 33.0 |

TABLE 1-continued

Adhesion Test results

| Compound | Co Addition level, parts per hundred rubber in skim stock | Unaged | Heat Aged | Humidity aged | Steam aged | Salt aged |
|---|---|---|---|---|---|---|
|  | 0.100 | 39.1 | 37.4 | 36.4 | 37.2 | 25.1 |
| Example 1 | 0.224 | 38.2 | 38.3 | 39.2 | 31.4 | 36.1 |
|  | 0.150 | 44.4 | 37.4 | 37.8 | 38.9 | 42.1 |
|  | 0.100 | 37.4 | 38.6 | 32.1 | 39.7 | 33.9 |
| Example 2 | 0.224 | 42.4 | 40.7 | 37.9 | 32.7 | 40.0 |
|  | 0.150 | 40.9 | 38.5 | 36.2 | 36.8 | 37.4 |
|  | 0.100 | 43.9 | 36.8 | 37.3 | 40.5 | 33.8 |
| Example 3 | 0.224 | 44.2 | 42.4 | 44.5 | 36.5 | 34.7 |
|  | 0.150 | 44.0 | 39.5 | 39.4 | 38.6 | 37.4 |
|  | 0.100 | 39.3 | 40.7 | 37.6 | 37.6 | 33.7 |
| Example 4 | 0.224 | 40.7 | 37.5 | 39.2 | 25.1 | 37.7 |
|  | 0.150 | 38.0 | 37.4 | 31.0 | 36.2 | 30.9 |
|  | 0.100 | 43.7 | 35.8 | 37.7 | 42.5 | 34.6 |

What is claimed is:

1. A metal organic compound of average formula

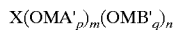

$$X(OMA'_p)_m(OMB'_q)_n$$

where X is aluminium, titanium, zirconium or silicon or alkyl- or aryl-silicon or dialkyl-, diaryl- or alkylaryl-silicon, M is cobalt or nickel, A' is a residue of an aliphatic carboxylic acid of 7 to 15 carbon atoms, B' is a residue of an aromatic carboxylic acid of 7 to 15 carbon atoms or an aliphatic or aromatic aryloxy carboxylic acid of 8 to 15 carbon atoms, p and q are, independently 0.5 to 1.5, m+n=x, wherein x is the valency of X.

2. A metal organic compound according to claim 1 in which M is Co(II).

3. A metal organic compound according to claim 1 or 2 in which B' is a residue of benzoic acid, 2-, 3- or 4-methyl benzoic acid, salicylic acid, 3,5-diisopropyl salicylic acid, 3,5-ditertbutyl salicylic acid, anthranilic acid, cinnamic acid, phenoxy acetic acid or phenoxy propionic acid.

4. A metal organic compound according to any one of claims 1 to 3 in which A' is a residue of neodecanoic acid, isoundecanoic acid, cekanoic acid or 2-ethyl hexanoic acid.

5. A metal organic compound according to any one of the preceding claims in which m/n is from 0.67 to 9.0.

6. A metal organic compound according to claim 5 in which m/n is from 1.5 to 4.0.

7. A metal organic compound as claimed in any one of claims 1 to 6 associated with up to 20% by weight of a borate of a metal of Group IA or IIA of the Periodic Table.

8. A metal organic compound as claimed in any one of claims 1 to 6 associated with microcrystalline wax, process oil or hydrocarbon resin or resorcinol/formaldehyde resin.

9. A metal organic compound claimed in any one of claims 1 to 6 supported on silica or a silicate of Group IA or IIA.

10. A rubber skim stock comprising rubber and, as an adhesion promoter, at least one metal organic compound as claimed in any one of claims 1 to 6.

11. A rubber skim stock according to claim 10 comprising 0.2 to 2.0 parts by weight of the said metal organic compound per hundred parts by weight of rubber.

12. Vulcanised rubber reinforced with brass coated steel comprising, as adhesion promoter, at least one metal organic compound as claimed in any one of claims 1 to 6.

* * * * *